United States Patent [19]

Hatcher et al.

[11] Patent Number: 4,927,757

[45] Date of Patent: May 22, 1990

[54] PRODUCTION OF SUBSTANTIALLY PURE FRUCTOSE

[75] Inventors: Herbert J. Hatcher, Idaho Falls; John J. Gallian, Twin Falls; Stephen A. Leeper, Idaho Falls, all of Id.

[73] Assignee: Idaho Research Foundation, Inc., Moscow, Id.

[21] Appl. No.: 225,914

[22] Filed: Jul. 29, 1988

[51] Int. Cl.$^5$ .................... C12P 19/02; C12P 19/24; C12P 19/18; C12N 11/18

[52] U.S. Cl. .................... 435/105; 435/94; 435/813; 435/175; 435/176; 435/101; 435/99; 435/97; 435/193

[58] Field of Search .................... 435/105, 101, 99, 97, 435/94, 193, 813, 175, 176

[56] References Cited

U.S. PATENT DOCUMENTS

| | | |
|---|---|---|
| 4,022,637 | 5/1977 | Sutthoff et al. |
| 4,096,036 | 6/1978 | Liu et al. |
| 4,276,379 | 6/1981 | Heady |
| 4,277,563 | 7/1981 | Kerkhoffs |
| 4,317,880 | 3/1982 | Heady |
| 4,335,207 | 7/1982 | Heady |
| 4,356,262 | 10/1982 | Heady |
| 4,769,254 | 9/1988 | Mays et al. |

FOREIGN PATENT DOCUMENTS 0142230 6/1986 European Pat. Off.

OTHER PUBLICATIONS

Y. Henis, "The Adaptive Formation of Levansucrase by a Species Corynebacterium" in *Journal of General Microbiology* (1956) 15:462–469.

Kim et al., "Separation of Fructose and Glucose by Reverse Osmosis" in *Ind. Eng. Chem. Fundam.* (1985) 24:409–412.

Adrian Fuchs "On the Synthesis and Breakdown of Levan by Bateria" (1959).

Gad Avigad et al., *Archives of Biochemistry and Biophysics* (1957) 70:178–184.

*Chem. Abstracts;* 102(17):147567y (1985).
*Chem. Abstracts;* 69(25):105374c (1968).
*Chem. Abstracts;* 85(5):30462z (1976).
*Chem. Abstracts;* 89(13):105914s (1978).
*Chem. Abstracts;* 103(21):175125s (1985).
*Biological Abstracts;* 85(4); 4117 (1988).
*Biological Abstracts;* 77(6); 44457 (1984).
*Biological Abstracts;* 67(5); 30508 (1979).
*Biological Abstracts;* 70(9); 60124 (1980).
*Biological Abstracts;* 64(7); 40832 (1977).
*Biological Abstracts;* 63(12); 69694 (1977).

*Primary Examiner*—Ronald W. Griffin
*Assistant Examiner*—Pamela S. Webber
*Attorney, Agent, or Firm*—Bertram I. Rowland

[57] ABSTRACT

A process is disclosed for the production of substantially pure fructose from sucrose-containing substrates. The process comprises converting the sucrose to levan and glucose, purifying the levan by membrane technology, hydrolyzing the levan to form fructose monomers, and recovering the fructose.

15 Claims, No Drawings

PRODUCTION OF SUBSTANTIALLY PURE FRUCTOSE

INTRODUCTION

1. Technical Field

This invention relates to two processes based on use of sucrose-containing substrates: the production of substantially pure levan and the production of substantially pure fructose.

2. Background of the Invention

As currently practiced, the commercial means of producing the sugar fructose or fructose-containing syrups is by the enzymatic isomerization of glucose obtained from starch hydrolyzates derived from corn. This is usually accomplished in a continuous process which involves contacting the glucose-containing solution with a glucose isomerase enzyme preparation that has been immobilized in some fashion. This process typically produces a syrup in which fructose is less than 50% of the total carbohydrate present.

Because fructose is sweeter than either glucose or sucrose, processes have been developed for producing syrups in which more than 50% of the carbohydrate is fructose. Typically, these methods have involved chromatographic procedures for separating the fructose from the other carbohydrates formed.

More recent efforts to obtain fructose syrup have utilized a fructosyl transferring enzyme to form fructose polymers and glucose. The glucose in the product can be isomerized to fructose by means of a glucose isomerase enzyme. Alternatively, another method utilized to remove contaminating glucose is fermentation of the fructose-glucose mixture with a yeast preparation which produces ethyl alcohol from the glucose ($\beta$-fructofurasidase).

RELEVANT LITERATURE

U.S. Pat. Nos. 4,277,563; 4,317,880; 4,356,262; 4,276,379; European Patent Applications Nos. 0,142,230; 0,011,350.

SUMMARY OF THE INVENTION

A process is disclosed for the production of substantially pure fructose from sucrose-containing substrates. The process comprises converting the sucrose to levan (a fructose polymer) and glucose, purifying the levan by membrane technology, hydrolyzing the levan to form fructose monomers, and recovering the fructose. The product can be obtained as a high fructose syrup of greater than 60% fructose or as a fructose crystalline sugar. Alternatively, the potentially useful carbohydrate, levan, can be the end-product of this process.

DESCRIPTION OF THE SPECIFIC EMBODIMENTS

In accordance with the subject invention, a process for the production of essentially pure levan or crystalline fructose and high fructose syrup, greater than 60% fructose, is provided. The instant process offers advantages over other practiced methods for the production of fructose as being both energy and cost efficient. First, any source of sucrose which is freed of solid matter can be utilized to form levan and glucose by the action of a fructosyl transferring enzyme, such as levan sucrase. Additionally, as opposed to current methods for the production of fructose which are very energy intensive due to evaporation procedures, the current invention greatly reduces processing cost for the production of fructose by a reduced need for evaporation because of initial concentration of the product by membrane technology. Membrane technology includes any method for purification or concentration by filtering such as ultrafiltration, hyperfiltration, diafiltration, etc.

A product of substantially pure fructose is recovered by the subject invention. The product may be obtained as a crystalline sugar of 95% or greater fructose or, alternatively, as a high fructose syrup, which is substantially free of glucose and sucrose, containing more than 60% fructose by weight. Variations for obtaining substantially pure forms of levan are also disclosed.

As utilized in the present invention, sucrose-containing substrate includes any substrate containing raw or refined sucrose. It includes mixtures of sucrose and varying amounts of other sugars, which have a sucrose content of at least 1%, preferably 100%, on a dry weight basis. Virtually any source of sucrose which has been substantially freed of solid matter can be utilized in the present invention including cane sugar, beet sugar, molasses, etc. Sucrose or cane sugar is a disaccharide of glucose and fructose. It is extremely abundant in the plant world and is familiar as table sugar.

Sucrose is converted to levan and glucose by the action of the fructosyl transferring enzyme. Fructosyl transferring enzyme refers to any enzyme that catalyzes transfructosylation, or the transfer of a fructose moiety of sucrose to another molecule (such as levansucrase). A specific reaction yields levan, a polysaccharide comprising 2 or more fructosyl units per molecule. Many such enzyme preparations are known including the enzyme prepared from *Microbacterium laevaniformans*, ATCC No. 15953. See also, Adriaan Fuchs, "On the synthesis and breakdown of levan by bacteria," Doctoral Thesis, University of Leiden, 1959.

Enzyme preparation refers to any composition of matter that exhibits the desired enzyme activity and is derived from any useful microorganisms or compositions equivalent thereto. The term "derived" is used to refer to enzyme activity obtained from live whole microbial cells, dry cells, cell extracts, and refined and concentrated preparations from cells and from culture liquors. Additionally, enzyme preparations include enzymes in solution or in an immobilized form. Immobilized enzyme refers to the physical or chemical coupling of the enzyme to essentially insoluble inert carrier materials which facilitate their use in flow-through reactors. When the immobilized enzyme is contacted with a liquid in which it is normally soluble, the enzyme remains attached to the carrier. Materials utilized for the carrier include organic and inorganic materials, such as those as set forth in U.S. Pat. No. 4,276,379, whose disclosure is herein incorporated by reference.

In the case where the sucrose is obtained directly from raw sugarbeets, the sucrose-containing substrate is purified as follows:

1. Crushed or shredded beets are agitated for one hour at the ratio of 100.0g to 250 ml of hot distilled or deionized water (60–70° C.) in which 1.0g calcium sulfate has been dissolved.
2. The beet pulp is removed from the resulting thin juice by straining and pressing.
3. The pH of the juice is adjusted to 5.6 with very dilute sulfuric acid, and 1.0 g of calcium oxide per each 50 ml is slowly added, while maintaining agitation at a temperature of 60–70° C.

4. Agitation and heat are continued, and after 5 minutes carbon dioxide is gently bubbled through the juice for 2 minutes.
5. After an additional 5 minutes, the resulting precipitate is filtered, leaving the purified juice.

In the case where the sucrose is obtained from sugarbeet molasses, the sucrose-containing substrate is partially purified as follows:
1. The molasses is first diluted 1:3, molasses:water, and heated to 60–70° C.
2. The remainder of the purification process is accomplished by following steps 3–5 described in the previous paragraph using the dilute molasses instead of thin juice.

The sucrose-containing substrate is treated with a fructosyl transferring enzyme to yield the intermediate products. The amount of enzyme utilized in the reaction may vary widely. Practical rates of reaction are observed when 10-30 fructosyl transferring enzyme units are used per gram of sucrose in the reaction mixture. Even higher rates of reaction are obtained by the use of larger amounts of enzyme. A fructosyl transferring unit is defined as the amount of enzyme activity required to produce one micromole of reducing sugar, calculated as glucose, per minute under the following conditions, pH 6.0–7.5, preferably 6.5, temperature 20° C., to 30° C., preferably 25° C. to 30° C., more preferably 25° C., and substrate concentration at 0.50 to 25 g sucrose per 100.0 ml of reaction mixture depending upon the membrane arrangement to be used. In batch processes, higher concentrations are necessary.

The starting sucrose substrate concentration can range from as low as 0.5 grams per 100 ml of water. However, it is preferable to employ as high a dry substance concentration of sucrose as possible, in a batch process, preferably ranging from about 10 grams to about 35 grams per 100 ml of solution.

The reaction is carried out at any convenient temperature below that which inactivates the fructosyl transferring enzyme. When the enzyme preparation is derived from a strain of *Microbacterium laevaniformans*, a temperature range from about 24° C. to 28° C., more preferably up to about 26° C., is employed. The pH of the reaction may vary from pH 6.0 to 7.0, preferably about 6.5.

An example of the present process for conversion of sucrose to a high fructose syrup can be divided into four subprocesses: (1) polymerization or converting the sucrose to levan and glucose; (2) purification/concentration of the intermediate product; (3) hydrolysis of levan to fructose monomers and smaller polymers; and (4) product recovery. Variations are possible within each separate subprocess as discussed below.

An example of the polymerization subprocess is the converting of sucrose to levan and glucose by the enzyme levansucrase. Since one of the byproducts, glucose, inhibits the synthesis of levan, continuous removal from the reaction can be beneficial. Glucose removal can be achieved by the use of bioreactor designs which provide for continuous byproduct removal. Such designs include, but are not limited to: (1) continuously stirred tank reactors (CSTR); (2) hollow-fiber membrane bioreactors (HFBR); and (3) coupled-CSTR-ultrafiltration-recycle bioreactors (CUFBR). Options (2) and (3) can be operated in continuous, semi-batch, or fed-batch modes. Although all three bioreactors provide for the removal of the inhibiting glucose byproduct, for the purposes of the present invention, the HFBR or CUFBR bioreactors are preferred as both systems allow the enzyme preparation and intermediates to be retained at an enhanced level relative to the byproducts. In these reactors, the cells and polymers are retained by a membrane while the glucose is removed from the system in a waste stream. A retentate stream consisting essentially of levan is collected. A portion of the retentate stream may be recycled into the bioreactor to utilize unreacted sucrose.

In the continuous byproduct method, sucrose reacts with the enzyme preparation yielding levan and glucose. As increasing amounts of glucose inhibit the synthesis of levan, the permeate is passed through a membrane filter removing glucose in a waste stream. At the same time, a stream of levan, the retentate stream, is collected. From the retentate stream, the enzyme preparation, or bacterial cells, can be recovered and returned to the reactor. Alternatively, it may be more cost efficient to continuously supply enzyme preparation from a separate enzyme preparation reactor.

The polymerization subprocess may also be performed in a batch mode. Batch systems include both a coupled batch system and a separated batch system. The coupled batch system allows for the continuous removal of inhibiting glucose leaving the levan, sucrose, and enzyme preparation in the reactor for a length of time to obtain optimum levels of levan. In a separated batch mode, the reaction continues for a time until inhibiting levels of glucose are obtained within the reaction mixture at which time the mixture is filtered and the levan is collected for further processing.

In the purification/concentration subprocess, the levan is purified and concentrated. An amount in the range of 10 to 15% w/v is optimum. Methods for purification include alcohol precipitation, ultrafiltration, diafiltration, hyperfiltration, reverse osmosis, solvent extraction, chromatography, liquid-liquid partition, and other forms of extraction. The laboratory scheme for levan purification involves repeated precipitation with alcohol and redissolution at high concentration. However, filtration and extraction methods are preferred for use in the present invention, as they are more amenable to industrial-scale processes. The filtering methods involve the separation of molecules on the basis of molecular weight and/or molecular size. Pressure is used to filter the aqueous medium and small solute molecules through a semi-permeable membrane which retains larger molecules. In the present invention, ultrafiltration and diafiltration are used to refer to filtering methods with the molecular weight (mw) cut-off from about 10,000 to 100,000, preferably about a 30,000 mw cut-off, with hyperfiltration, or reverse osmosis, being used to specify the separation of much smaller sized molecules. Hyperfiltration refers to an mw cut-off of up to and including 500 mw.

The membranes utilized comprise polymeric materials, such as cellulose, acetates, polysulfones, and polyamides. Ceramic materials such as aluminum oxides may also be used. The membrane permeability can be altered by the method of membrane casting as well as the mode of operating the filtration system. For purposes of the present invention, the purification/concentration subprocess is accomplished by any one or by any combination of the purification methods. The same purification method may be repeated if necessary, i.e. several ultrafiltration steps, or different methods can be employed, i.e., ultrafiltration followed by hyperfiltration or reverse osmosis.

In the hydrolysis subprocess, purified levan is hydrolyzed to produce a fructose stream of about 1 to 20% fructose. Hydrolyzing agents and conditions for hydrolysis are chosen so that the resulting fructose is not destroyed. The hydrolysis reaction may be catalyzed by either acid or enzymatic methods. For the enzymatic preparation of fructose from levan, the enzyme levanase, a well known commercially available enzyme, is capable of hydrolyzing levan to form fructose monomers and oligomers. An advantage to enzymatic hydrolysis is that the reaction can be carried out in a mild acid to neutral medium, thereby avoiding the formation of the byproducts often formed in acid hydrolysis. The enzyme, levanase, may be used in a soluble or immobilized form. A membrane bioreactor may be used to retain levan and enzymes and not retain fructose. The activity of the enzyme preparation is expressed in standard units, one unit being the activity required to produce one micromole of fructose per minute from levan at 50° C. and pH 6.5. The amount of enzyme preparation utilized in the reaction depends upon the concentration of levan, the activity of the enzyme preparation, and the time available for the reaction. In most cases, an amount of enzyme preparation corresponding to an activity of more than 10 units, more particularly about 10 to 100 units per gram of levan contained in the solution will be utilized.

The temperature and pH of the reaction are altered to optimize enzymatic activity. The pH will generally range from about 4.5 to about 5.5, more particularly 5.0. The temperature may be varied during the reaction and includes any temperature at which the enzyme is not inactivated. Generally, the temperature will range from about 45° C. to about 55° C., preferably about 50° C.

The reaction is carried out in an aqueous medium by mixing purified levan and the enzyme preparation. Water may be added to adjust the levan concentration. The enzymatic preparation may be added at the beginning of the reaction or in portions as the reaction proceeds. The reaction may be carried out in a single stirred reactor or in a series of stirred reactors. In another embodiment, the levan can be hydrolyzed by passing the levan solution through a membrane filter containing an immobilized enzyme preparation of levanase.

Acid hydrolysis is accomplished by the addition of an acid to form a dilute acid solution and heating. Acids for the hydrolysis step include any dilute acid, preferably mineral acids such as sulfuric acid or phosphoric acid. Acid hydrolysis is rapid but must be carefully controlled to avoid product degradation. Generally an amount of acid is added to the levan solution for a final concentration from about 0.025 to about 0.075 M, preferably about 0.05 M. The solution is heated to a temperature ranging from about 60° C. to about 90° C., preferably about 70° C. to about 75° C. In batch mode, the hydrolysis reaction is monitored and the reaction stopped when the yield is optimized. Continuous hydrolysis can also be used.

In the product recovery subprocess, fructose is recovered and concentrated. Recovery methods include, but are not limited to, diafiltration, hyperfiltration, reverse osmosis, evaporation, drying, crystallization, chromatography, and the like. Any one or combination of the methods may be employed. For a final product of high fructose syrup, hyperfiltration or reverse osmosis is utilized as the preconcentration step, followed by evaporation. Evaporation is accomplished by standard sugar solution evaporation methods. After hyperfiltration, the fructose stream is heated to a temperature of about 70° C. to about 80° C. for a period of time giving the product concentration desired. The use of hyperfiltration or reverse osmosis before separation dramatically reduces the energy requirements of high fructose syrup production by reducing the energy consumed by evaporation. Fructose remaining in the hydrolysis waste stream can be recovered by diafiltration and recycled to the fructose product stream for hyperfiltration and/or evaporation. For the production of a crystalline product, the high fructose syrup can be dried by most known drying methods for the production of sugar crystals.

Limitations on drying methods are dictated by the heat-sensitivity of the product. Fructose is more heat-labile than most sugars. Low holdup and short contact times as well as low temperatures are required. In general, a film-type evaporation should be used. In particular, an agitated thin-film evaporator or a spray dryer are most suitable. The material of construction should be 304 or 316 stainless steel. The liquid film temperature in a thin-film evaporator should not exceed 80° C. In spray drying, the particle size should be between 10 and 60 microns. The temperature of the particle should not exceed 100° C. and cool air should be admitted at the drying chamber walls to prevent the product from sticking to the walls.

Another embodiment of the inventive process includes the production of high fructose syrup as follows: (1) Levan is formed from sucrose as previously described, including partial glucose and sucrose removal, (2) Levan is hydrolyzed to fructose enzymatically, (3) The catalyst and other particulate matter is removed by centrifugation or other appropriate methods, and (4) The soluble sugars are concentrated to produce a high fructose syrup of 60% or greater.

Another product of the present invention is levan. Levan in a substantially pure form may find application as a food additive or thickening agent for liquid products. Additionally, levan has attracted attention because of a number of biological activities including infection promoting activity, endothelial sealing activity, and properdin-binding power. Substantially pure levan may be obtained by following the subprocess steps outlined above, but omitting the hydrolysis subprocess.

The following examples are offered by way of illustration and not by way of limitation.

EXPERIMENTAL

EXAMPLE 1

CUFBR Production of Levan

A 2.0 liter reactor is fitted with inlet and outlet tubes so that the reaction mixture can be continuously pumped from the reactor through an ultrafiltration apparatus with the majority of the retentate being recycled back to the reactor. The sucrose-containing substrate, pre-treated juice from crushed sugarbeets, is placed in the reactor at a sucrose concentration of about 3 to 15%. The fermentation medium includes $K_2HPO_4$-0.3% w/w, NaCl-0.5% w/w, $NH_4Cl$-0.2% w/w, and yeast extract-1.5% w/w. The pH of the solution is adjusted to 6.5 and maintained at this pH throughout the reaction by the addition of 0.5 M sodium hydroxide solution as needed.

*Microbacterium laevaniformans* is grown on nutrient agar, harvested, resuspended, and the suspension diluted to 0.10–0.20 optical density. Of this suspension, 5–10 ml is used to inoculate 500 ml in a baffled Erlenmeyer flask. The cells are grown at 30° C. for 20 to 24 hours. The cells are harvested by centrifugation, resuspended, and added to the levan production medium containing 0.5% to 30% sucrose and 0.3% yeast extract. After addition of the bacterial suspension, the levan production medium is agitated at 26° C. to 28° C. and the reaction is allowed to proceed for 4 hours without the removal of permeate. After 4 hours of reaction, the product from the reactor is cycled though the ultrafiltration apparatus. At this point, a stream containing glucose and unreacted sucrose is collected separately. Sucrose may be recovered and recycled. A retentate stream containing levan, unreacted sucrose, and residual glucose is returned to the stirred bioreactor. A fraction of the retentate stream is removed before recycle, and becomes the product stream. The product stream is then subjected to further processing.

EXAMPLE 2

Use of Immobilized Enzyme

A sucrose solution and medium as set forth in Example 1 is placed in a reservoir tank which is fitted with inlet and outlet tubes so that the reaction mixture is continuously pumped from the reservoir tank into a bioreactor. From the bioreactor, the mixture is passed through an ultrafiltration apparatus as set forth in Example 1, but additionally containing immobilized enzyme, levansucrase, in the ultrafiltration apparatus. Thus, the ultrafiltration device provides for the removal of glucose and additionally for the formation of levan. The glucose waste stream is collected and the majority of the retentate stream is recirculated back into the reservoir tank. A portion of the retentate stream is collected as product.

EXAMPLE 3

Acid Hydrolysis of the Product

Acid hydrolysis of the product levan from Examples 1 and 2 is carried out by the addition of sulfuric acid to a concentration of 0.05 M at a temperature of 75° C.–80° C. for a period of 2 hours.

EXAMPLE 4

Enzyme Hydrolysis of the Product

The products from Examples 1 and 2 are collected in an HFBR containing the immobilized enzyme levanase contained within the ultrafiltration device. The pH of the mixture is adjusted to 5.0 with 5 M phosphoric acid. Although the temperature may be varied for the reaction, the temperature is held at 28° C. The reaction is pumped through the ultrafiltration device where the immobilized enzyme hydrolyzes the levan to form fructose monomers and smaller polymers.

EXAMPLE 5

Fructose Recovery

The fructose stream from Example 4 is collected in a reservoir tank and then passed through a hyperfiltration or reverse osmosis apparatus where it is concentrated. The fructose solution is then subjected to evaporation to produce a high fructose syrup containing 60% fructose.

All publications and patent applications mentioned in this specification are indicative of the level of skill of those skilled in the art to which this invention pertains.

All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A process for the production of a substantially pure product containing greater than 60% fructose, comprising:
    combining a sucrose-containing substrate with effective amounts of a levansucrase enzyme preparation to form levan and glucose;
    purifying said levan by at least one of the following purification methods: ultrafiltration, diafiltration, hyperfiltration, reverse osmosis, liquid-liquid partition, solvent extraction, chromatography, and precipitation;
    hydrolyzing said levan to form fructose substantially free of glucose and sucrose; and,
    recovering said fructose by at least one of the following recovery methods: hyperfiltration, reverse osmosis, evaporation, drying, crystallization, and chromatography.

2. The process, as recited in claim 1, wherein said combining step further comprises a method for the continuous removal of glucose.

3. The process, as recited in claim 1, wherein said levansucrase enzyme preparation is derived from *Microbacterium laevaniformans*, ATCC No. 15953.

4. The process, as recited in claim 1, wherein said hydrolyzing step further comprises:
    hydrolyzing said levan in an acidic solution.

5. The process, as recited in Claim 1, wherein said acidic solution comprises an acid selected from the group consisting of sulfuric acid and phosphoric acid.

6. The process, as recited in claim 1, wherein said hydrolyzing step further comprises:
    hydrolyzing said levan by enzyme hydrolysis.

7. The process, as recited in claim 1, wherein said enzyme is levanase.

8. The process, as recited in claim 1, wherein subjecting is at a temperature in the range of about 20° C. to 30° C. and a pH in the range of about 6.0 to 7.5 and said hydrolyzing is by enzymatic hydrolysis at a temperature in the range of about 45° C. to 55° C. and a pH of about 4.5 to 5.5.

9. The process, as recited in claim 1, wherein subjecting is at a temperature in the range of about 20° C. to 30° C. and a pH in the range of about 6.0 to 7.5 and said hydrolyzing is by dilute acid hydrolysis at a temperature in the range of about 60° C. to about 90° C. and at a concentration in the range of about 0.025 to 0.075 N.

10. The process, as recited in claim 1, wherein said sucrose-containing substrate is purified juice from crushed or shredded sugarbeets or diluted, partially purified, sugarbeet molasses.

11. A process for the production of a substantially pure levan product comprising:
    subjecting a sucrose-containing substrate to effective amounts of a levansucrase enzyme preparation to form levan and glucose, while continuously removing glucose; and purifying said levan by at least one of the following purification methods: ultrafiltration, diafiltration and hyperfiltration.

12. A process for the production of a substantially pure product containing greater than 60% fructose, comprising:

combining a solution containing 0.5 to 30 g of sucrose per 100 ml solution with a levansucrase enzyme preparation containing 10 to 30 fructosyl transferring units per gram of sucrose to form levan and glucose;

purifying said levan by at least one of the following purification methods; ultrafiltration, diafiltration, hyperfiltration, reverse osmosis, liquid-liquid partition, solvent extraction, chromatography or precipitation;

hydrolyzing said levan to form fructose substantially free of glucose and sucrose; and recovering said fructose by at least one of the following recovery methods; hyperfiltration, reverse osmosis, evaporation, drying, crystallization, or chromatography.

13. The process, as recited in claim 12, wherein said combining step further provides for the continuous removal of glucose.

14. The process, as recited in claim 12, wherein said hydrolyzing step comprises contacting said levan with an acidic solution at a temperature of about 75° C. for a period of at least two hours.

15. The process, as recited in claim 14, wherein said acid is selected from sulfuric acid and phosphoric acid.

* * * * *